US00PP17314P2

(12) United States Plant Patent

Keogh et al.

(10) Patent No.: US PP17,314 P2
(45) Date of Patent: Dec. 26, 2006

(54) *CALLISTEMON* PLANT NAMED 'MATTHEW FLINDERS'

(50) Latin Name: *Callistemon viminalis*
Varietal Denomination: Matthew Flinders

(76) Inventors: Terry Keogh, 209 Bunker Road, Victoria Point, Queensland (AU), 4165; Jocelyn Mary Keogh, 209 Bunker Rd, Victoria Pt, Q'ld (AU), 4165

( * ) Notice: Subject to any disclaimer, the term of this patent is extended or adjusted under 35 U.S.C. 154(b) by 37 days.

(21) Appl. No.: 11/208,334

(22) Filed: Aug. 18, 2005

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

Plant Varieties Journal Quarter 3, 2003, vol. 16, No. 3, pp. 13, 32–33 [online], [retrieved on May 4, 2006]. Retrieved from the Internet <http:www.ipaustralia.gov.au./pbr/index.shtml>.*
Upov–rom Plant Variety Database 2005/04 GTI Jouve Retrievla Software, Citation for *Callistemon* 'Matthew Flinders'.*

* cited by examiner

*Primary Examiner*—Kent Bell
*Assistant Examiner*—June Hwu

(57) ABSTRACT

A new variety of *Callistemon viminalis* plant named 'Matthew Flinders' that is characterized by dwarf and compact habit, fine leaves and numerous bright red "bottle brush" type flowers. In combination these traits set 'Matthew Flinders' apart from all other existing varieties of *Callistemon* known to the inventor.

2 Drawing Sheets

Genus: *Callistemon*. Species: *viminalis*.
Denomination: 'Matthew Flinders'.

BACKGROUND OF THE INVENTION

The present invention relates to a new and distinct variety of *Callistemon* commonly called "Bottlebrush" that is grown and used as a hedging plant or used as a feature plant in ornamental containers. The new variety is known botanically as *Callistemon viminalis* and will be referred to hereinafter by the variety name 'Matthew Flinders'.

*Callistemons* are evergreen trees or shrubs of the family Myrtaceae which are native to Australia. Taller forms are used as street trees in frost-free regions of the United States, especially in coastal southern California. Two widely distributed forms of *Callistemon* are *Callistemon viminalis* 'Captain Cook' (unpatented) and *Callistemon viminalis* 'Little John' (unpatented) both of which have been in commerce for approximately thirty years. *Callistemon* 'Captain Cook' is grown for its ability to form a shrub whose spread is similar to its height, namely approximately 2 meters at maturity. *Callistemon* 'Little John' is of similar proportions but only achieves a mature height of approximately 1 meter.

In the early 1990s, the inventor carried out a deliberate cross between *Callistemon* 'Captain Cook' as seed parent with *Callistemon* 'Little John' as pollen parent. Seed from this cross was sown to produce $F_1$ seedlings which were then planted out of doors in a field trials bed at the inventor's nursery in Queensland, Australia. The established plants were allowed to flower and selectively used for a second round of crosses. For the second round of crosses, the inventor selected prospective male and female parents based on their field performance, especially promising combinations of dwarfness of habit, dense fine-leaved foliage, and number and brilliance of the characteristic red "bottle brush" flowers. The inventor collected seed from the second round of successfully pollinated parents. The collected seed was sown out of doors and the resulting seedlings were transplanted in the field in 1993 and allowed to grow naturally.

The inventor selected 'Matthew Flinders' in 1995 as a single whole plant from amongst the field population of second generation crosses. The inventor considered that 'Matthew Flinders' possessed unique characteristics in combination, namely a dwarf, dense and compact growth habit comprised of attractive fine green leaves and numerous bright red "bottle brush" type flowers.

When compared with the original male parent, *Callistemon* 'Little John', 'Matthew Flinders' is of similar size, shape and habit, but exhibits fine green leaves (137A on The Royal Horticultural Society Colour Chart), whereas the leaves of *Callistemon* 'Little John' are approximately 30% to 40% longer and 30% to 40% wider than the leaves of 'Matthew Flinders' and of a more grayed-green coloration (189A on The Royal Horticultural Society Colour Chart).

When compared with the original female parent, *Callistemon* 'Captain Cook', 'Matthew Flinders' is shorter and grows with a denser habit. *Callistemon* 'Captain Cook' develops an open habit as growth proceeds. The leaves of *Callistemon* 'Captain Cook' are 50% longer than the leaves of 'Matthew Flinders' although the width of the leaves of both varieties are similar, as is the color of the leaves.

The most similar variety to 'Matthew Flinders' known to the inventor is the male parent *Callistemon* 'Little John'. 'Matthew Flinders' differs from *Callistemon* 'Little John' as set forth above, and also in exhibiting a reddish color of bud prior to the opening of the flower spike, whereas the buds of *Callistemon* 'Little John' are green in color at this stage.

The inventor carried out the first asexual reproduction of 'Matthew Flinders' in 1997 at the inventor's propagation nursery at Wellington Point, Queensland, Australia, by rooting softwood cuttings taken from the originally selected single plant 'Matthew Flinders'. All of the resulting plants exhibited the typical characteristics of 'Matthew Flinders'. The inventor has determined from successive generations of asexual reproduction that the new variety 'Matthew Flinders' is stable and reproduces true to type.

An application for a grant of Australian Plant Breeders Rights for 'Matthew Flinders' has been filed as application number 2003/179 which was accepted for publication on Aug. 25, 2003. The application is pending at the Plant Breeders Rights Office of Australia.

The first sale or public distribution of 'Matthew Flinders' took place on Sep. 1, 2004.

SUMMARY OF THE INVENTION

The following traits have been repeatedly observed and represent the characteristics of the new variety 'Matthew Flinders'. These traits in combination distinguish this variety from all other commercial varieties known to the inventor. 'Matthew Flinders' has not been tested under all possible conditions and phenotypic differences may be observed with variations in environmental, climatic and cultural conditions.

1. 'Matthew Flinders' has dwarf and dense growth habit.
2. 'Matthew Flinders' has lanceolate leaves which are approximately 30 mm to 35 mm in length, and approximately 6 mm in width.
3. The leaves of 'Matthew Flinders' are fine textured and green in color.
4. The buds of 'Matthew Flinders' are red in color prior to opening of flower spike.
5. The inflorescence of 'Matthew Flinders' is comprised of numerous exserted stamens which give the appearance of a bright red flower spike.
6. The inflorescences of a plant of 'Matthew Flinders' are sufficiently numerous as to virtually obscure the foliage of 'Matthew Flinders' at peak flowering stage.

BRIEF DESCRIPTION OF THE DRAWINGS

The accompanying color drawings, labeled as FIG. 1 and FIG. 2 illustrate the overall appearance of the new *Callistemon* cultivar 'Matthew Flinders', showing the colors as true as it is reasonably possible to obtain in colored reproductions of this type. Colors in the drawings may differ from the color values cited in the detailed botanical description, which accurately describe the actual colors of the new variety.

The plant of 'Matthew Flinders' illustrated in FIG. 1 is approximately 12 months old from a cutting and has been grown out-of-doors in a 3 liter container in Queensland, Australia.

FIG. 1 also shows the early signs of the red coloration which becomes apparent on the buds of 'Matthew Flinders' prior to opening of the flower spike.

Figure 1:
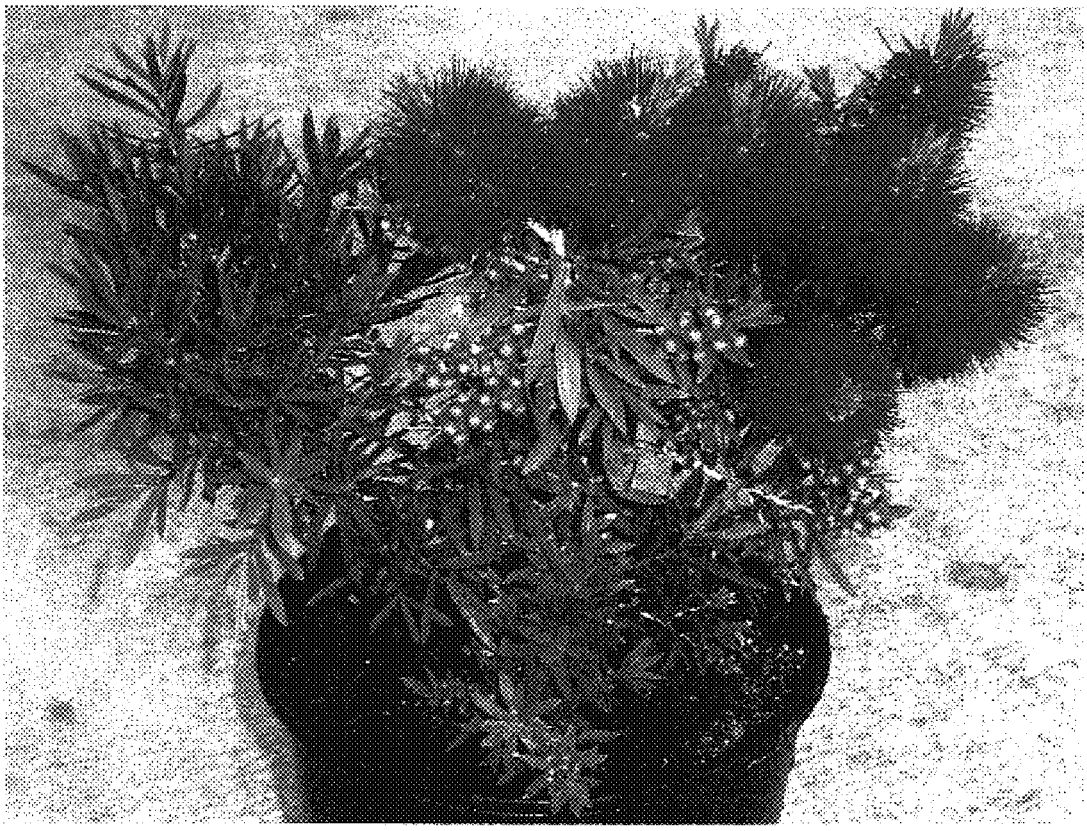
FIG. 1 shows the fine green leaves and cluster of bright red flowers.
Figure 2:
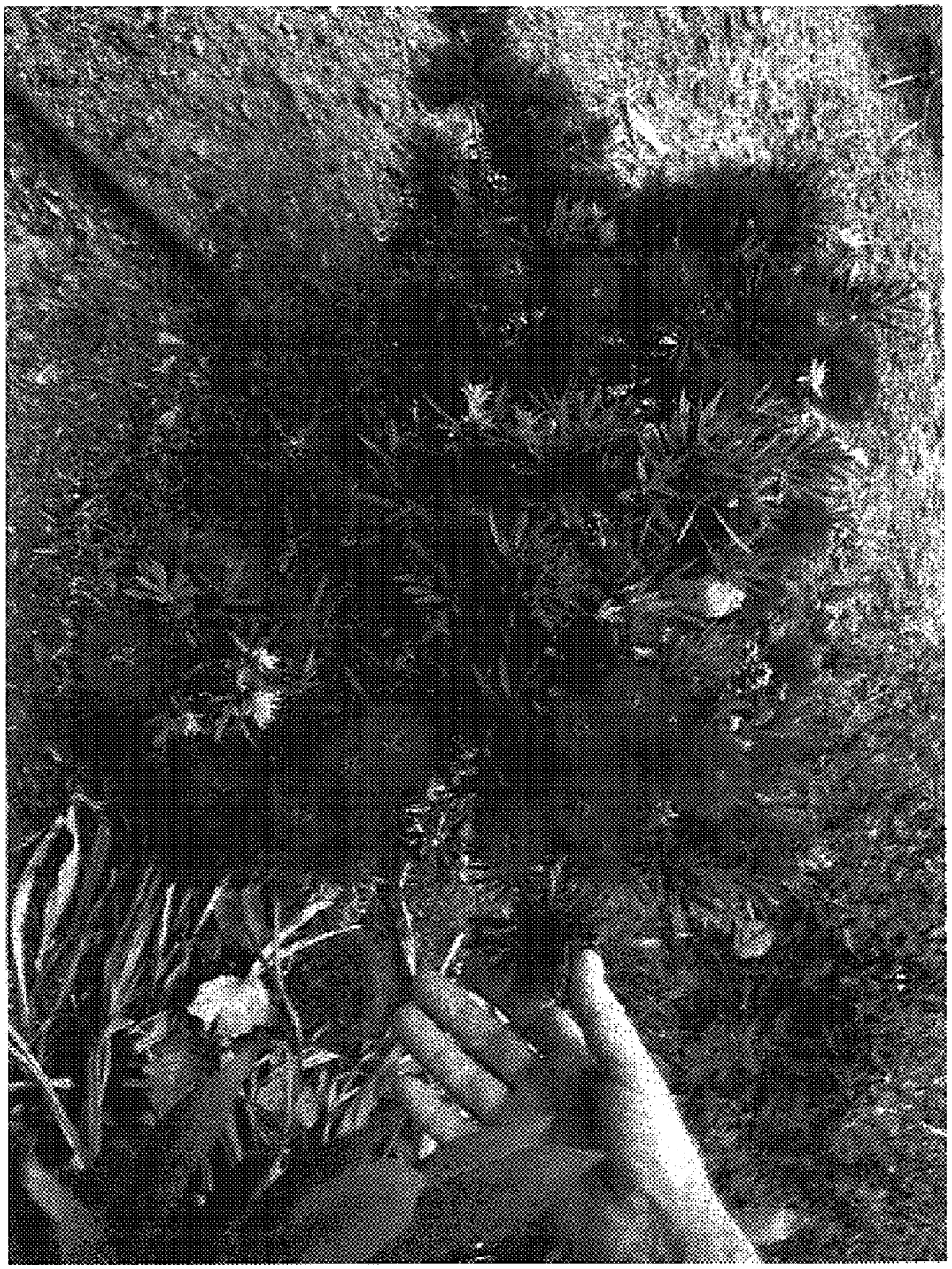

The plant of 'Matthew Flinders' illustrated in FIG. 2 is approximately 14 months old from a cutting and has been grown out of doors in the field in Queensland, Australia.

FIG. 2 illustrates the numerous flower spikes which virtually obscure the foliage of 'Matthew Flinders' at this stage.

BOTANICAL DESCRIPTION OF THE PLANT

The following is a description of the new variety 'Matthew Flinders'. Data was collected from plants grown in outdoor conditions at Redland Bay, Queensland, Australia., and which were approximately 12 months of age when in flower.

The colour determinations are in accordance with the 1995 Edition of The Royal Horticultural Society Colour Chart, London, England, except where general color terms of ordinary dictionary significance are used.

Growing and cultural requirements: Similar to other *Callistemon,* namely plant in full sun or partial shade. 'Matthew Flinders' is tolerant of a wide range of soil types and moisture levels.

Botanical classification: *Callistemon viminalis* 'Matthew Flinders'.

Commercial classification: Shrub for planting in the landscape shrub or in containers.

Common name: Bottle Brush.

Use: Ornamental for hedging or in containers.

Parentage: Unnamed parents resulting from the controlled pollination of *Callistemon* 'Captain Cook' as seed parent, and *Callistemon* 'Little John' as pollen parent.

Plant description:

*Bloom period.*—Spring.
*Plant habit.*—Upright, dwarf and dense.
*Height.*—1 m at maturity.
*Width.*—1 m at maturity.
*Hardiness.*—USDA Zone 8 to 11.
*Propagation.*—Propagation is accomplished using softwood cuttings. Roots well without rooting compound or hormone.
*Time to develop roots.*—4 to 8 weeks, when rooted on a heated bench.
*Crop time.*—From four to six months are needed to produce a 14-centimeter container with plant in flower, starting from a rooted cutting.
*Pest and disease susceptibility or resistance.*—In common with the species, none of note.

Stem:

*Shape.*—Cylindrical.
*Stem color.*—Young stem is grey red, closest to 178C.
*Stem dimensions.*—75 cm in length and 0.5 cm. in diameter.
*Stem surface.*—Papery or corky.
*Basal stem color.*—Juvenile growth: 153D becoming gray-orange 165C at maturity.
*Branching and habit.*—Strong branching habit; upright growth habit.
*Inter-node length.*—0.5 cm. to 0.75 cm.

Foliage:

*Type.*—Evergreen.
*Shape.*—Lanceolate.
*Division.*—Simple.
*Apex.*—Acute.
*Base.*—Acute.
*Venation.*—Pinnate.
*Vein color* (*adaxial surfaces*).—137A.
*Vein color* (*abaxial surfaces*).—137B.
*Margins.*—Entire.
*Arrangement.*—Whorled.

*Attachment.*—Sessile.
*Texture.*—Leathery.
*Surfaces* (*adaxial and abaxial*).—Finely pubescent to glabrous.
*Mature leaf dimensions.*—Mean length 32.4 mm, mean width 5.9 mm.
*Leaf color* (*adaxial surface*).—Juvenile: 144A; mature: 137A.
*Leaf color* (*abaxial surface*).—Juvenile: 144B; mature: 137B.
*Petiole.*—None.
*Stipules.*—None.

Inflorescence: Aggregate of spikes comprised of many exserted stamens which obscure the flowers.

*Spike.*—Shape: Oblong, cylindrical. Dimensions: 4 cm. to 6 cm in length and 4.5 to 5.5 cm in diameter (at maturity). Number of spikes in an inflorescence: 15–25. Persistent or self-cleaning: Self-cleaning. Attachement: Sessile. Aspect: Horizontal. Color (presented by exserted stamens and stigma): 46B. Fragrance: None.
*Flowers.*—Minute; corolla comprised of petals appearing to be five in number, ovate, unfused, transparent, color approximates to 150A or 150B, except margin 48B.
*Bud.*—Shape: Conical. Dimensions: Length 6 to 8 mm, width 3 to 4 mm. Color: Prior to reflexing of petals: 63B.
*Calyx.*—Inconspicuous.
*Sepals.*—As for calyx.

Reproductive organs:

*Stamens.*—Many in number, of the order of 100.
*Stamen color.*—46B.
*Stamen dimensions.*—About 2 cm. in length and very thin.
*Attachment.*—Each stamen joins floral tube independently: Free.
*Anther dimensions.*—Minute.
*Anther color.*—Yellow.
*Pollen.*—Present.
*Amount of pollen.*—Moderate amount.
*Color of pollen.* —Yellow.
*Pistil.*—One.
*Pistil dimensions.*—About 2.5 cm. in length and very thin.
*Pistil color.*—46B.
*Ovary position.*—Inferior.

Fruit and seed production: Dehiscent flowers leave persistent sessile seed capsules grouped tightly along stem.

*Capsules.*—Spherical, approximately 3 mm diameter. Color (immature): ranges between 143B and 143C. Color (mature) 122A or darker.
*Seeds.*—Minute, non-endospermic, mid-brown.

It is claimed:

1. A new and distinct variety of *Callistemon viminalis* plant named 'Matthew Flinders' as described and illustrated herein.

* * * * *